US006383806B1

(12) United States Patent
Rios

(10) Patent No.: US 6,383,806 B1
(45) Date of Patent: May 7, 2002

(54) METHOD FOR THE DEVELOPMENT OF AN HIV VACCINE

(76) Inventor: Adan Rios, 4007 Shallow Pond Ct., Sugar Land, TX (US) 77479

( * ) Notice: Subject to any disclaimer, the term of this patent is extended or adjusted under 35 U.S.C. 154(b) by 0 days.

(21) Appl. No.: 09/249,391

(22) Filed: Feb. 12, 1999

Related U.S. Application Data

(60) Provisional application No. 60/074,646, filed on Feb. 13, 1998.

(51) Int. Cl.$^7$ .............................. C12N 5/06; C12N 5/00; C12Q 1/70; G01N 33/53
(52) U.S. Cl. ..................... 435/339.1; 435/5; 435/7.1; 435/325
(58) Field of Search ........................ 435/5, 7.1, 325, 435/339.1

(56) References Cited

U.S. PATENT DOCUMENTS

| | | | |
|---|---|---|---|
| 5,849,475 A | 12/1998 | Rovinski et al. | 435/5 |
| 5,919,458 A | 7/1999 | Aldovini et al. | 424/188.1 |
| 6,017,543 A | 1/2000 | Salk et al. | 424/208.1 |
| 6,080,408 A | 6/2000 | Rovinski et al. | 424/188.1 |

OTHER PUBLICATIONS

Rossio et al., "Inactivation of Human Immunodeficiency Virus Type 1 Infectivity with Preservation of Conformational and Functional Integrity of Virion Surface Patterns," *J. Virology*, 72(10):7992–8001, 1998.
Sylwester et al., "CD4$^+$ T–Lymphocyte Depletion in Human Lymphoid Tissue Ex Vivo Is Not Induced by Noninfectious Human Immunodeficiency Virus Type 1 Virions," *J. Virology*, 72(11):9345–9347, 1998.
Zhang et al., "Nascent Human Immunodeficiency Virus Type 1 Reverse Transcription Occurs within an Enveloped Particle," *J. Virology*, 69(6):3675–3682, 1995.

Albert, et al., "Dendritic cell acquire antigen from apoptotic cells and induce class I–restricted CTLs," *Nature*, 392:86–89, 1998.
Balter, "Modest briton stirs up storm with views on role of CTLs," *Science*, 280:1860–1861, 1998a.
Balter, "Duo brings hope of immune restoration," *Science*, 280:1861, 1998b.
Balter, "A cluster of Euorope's aids research stars," *Science*, 280:1862, 1998c.
Balter, "Global program struggles to stem the flood of new cases," *Science*, 280:1863–1864, 1998d.
Balter, "HIV incidence: 'more serious than we imagined'," *Science*, 280:1864, 1998e.
Cavert and Haase, "A national tissue bank to track HIV eradication and immune reconstitution," *Science*, 280:1865–1866, 1998.
Daniel, et al., "A role for DNA–PK in retroviral DNA integration," *Science*, 284:644–647, 1999.
Emerman and Malim, "HIV–1 regulatory/accessory genes: keys to unraveling viral and host cell biology," *Science*, 280:1880–1884, 1998.
Guidotti, et al., "Viral clearance without destruction of infected cells during acute HBV infection," *Science*, 284:825–829, 1999.
Harouse, et al., "Distinct pathogenic sequela in rhesus macaques infected with CCR5 or CXCR4 utilizing SHIVs," *Science*, Internet: www.sciencemag.org, 1999.
Ho, "Toward HIV eradication or remission: the tasks ahead," *Science*, 280:1866–1867, 1998.

(List continued on next page.)

Primary Examiner—Hankyel T. Park
(74) Attorney, Agent, or Firm—Fulbright & Jaworski L.L.P.

(57) ABSTRACT

Human immunodeficiency virus (HIV) comprising reverse transcriptase inactivated by photoinactivation used to evoke an immune response. The immune response may protect an individual from challenges with live virus. Alternatively, the inactivated HIV particles may be used to augment the immune response to HIV in an infected individual.

17 Claims, 1 Drawing Sheet

OTHER PUBLICATIONS

Figure 1:
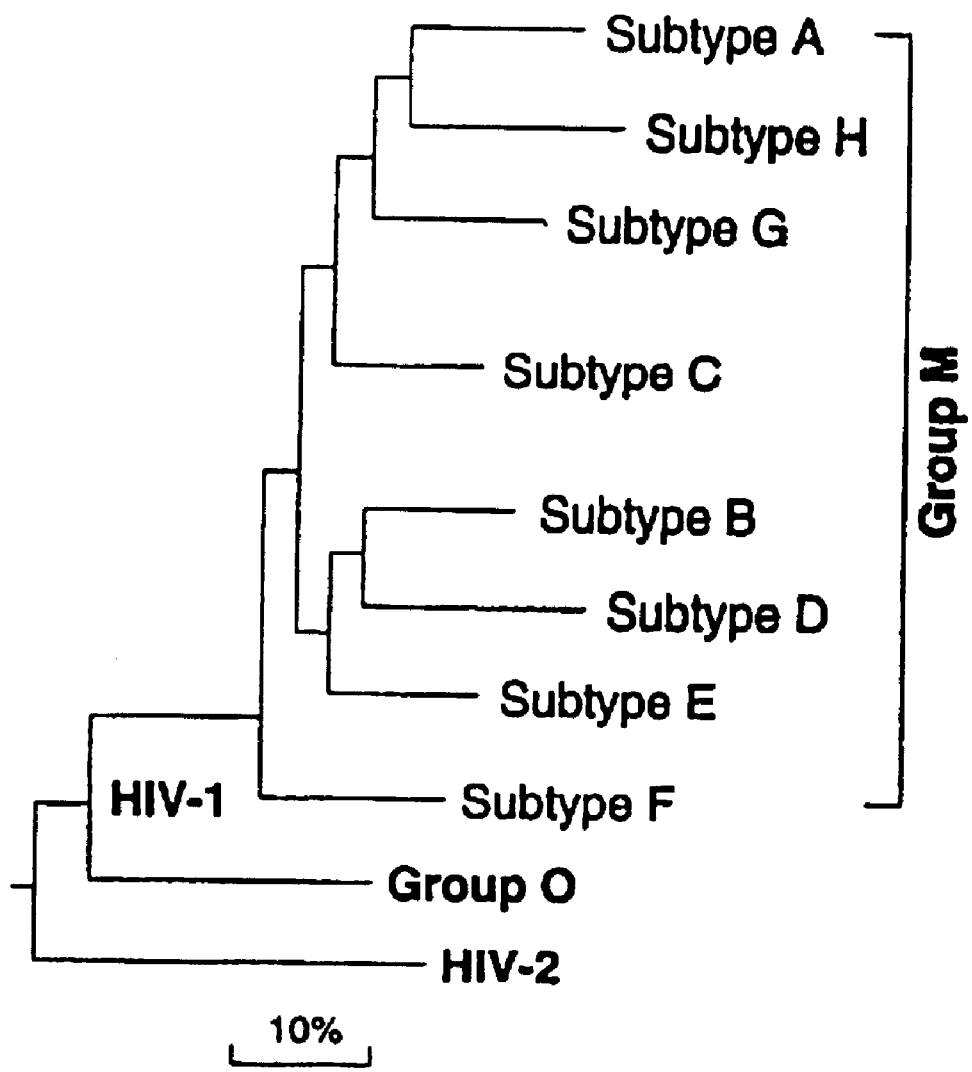

Korber, et al., "Limitations of a molecular clock applied to considerations of the origin of HIV–1," *Science*, 280:1868–1871, 1998.

Letvin, "Progress in the development of an HIV–1 vaccine," *Science*, 280:1875–1880, 1998.

MIMH Trial Group, "The NIMH multisite HIV prevention trial: reducing HIV sexual risk behavior," *Science*, 280:1889–1894, 1998.

Perrin and Telenti, "HIV treatment failure: testing for HIV resistance in clinical practice," *Science*, 280:1871–1873, 1998.

Phoolcharoen, "HIV/aids prevention in Thailand: success and challenges," *Science*, 280:1873–1874, 1998.

Tang and Cyster, "Chemokine up–regulation and activated T cell attraction by maturing dendritic cells," *Science*, 284:819–822, 1999.

Walker, "Immunopathogenesis and immune reconstitution in HIV disease," *Intl. Aids Soc.–USA*, 6:4–7, 1999.

Wyatt and Sodroski, "The HIV–1 envelope glycoproteins: fusogens, antigens, and immunogens," *Science*, 280:1884–1888, 1998.

"Aronex HIV inhibitor nears patent issuance," *Reuters New-Media, Inc.*, Feb. 23, 1996, Abstract.

"Aronex reports preliminary clinical results on its HIV integrase inhibitor, zintevir (TM)," *PR Newswire*, Nov. 12, 1996, Abstract.

Ada, "Modern vaccines, the immunological principles of vaccination," *The Lancet*, 335:523–526, 1990.

Ada, "An Immunologist's View of HIV Infection," *Textbook of AIDS Medicine*, Chapter 6, pp. 77–87, Brother et al., eds., Williams & Wilkens, Baltimore, MD, 1994.

Aldrovandl et al., "The SCID–hu mouse as a model for HIV–1 infection," *Nature*, 363:732–736, 1993.

Amadori et al., "The hu–PBL–SCID mouse in human lymphocyte function and lymphomagenesis studies: achievements and caveats," *Semin Immunol*, 8:249–254, 1996.

Baba et al., "Pathogenecitiy of live, attenuated hiv after mucosal infection of neonatal macaques," *Science*, 267:1820–1825, 1995.

Bachmann and Zinkernagel, "Neutralizing antiviral b cell responses," *Annu. Rev. Immunol.*, 15:235–270, 1997.

Balter, "T cell production slowed, not exhausted?" *Science*, 283(5400):305–306, 1999.

Baltimore, "Lessons from people with nonprogressive hiv infection," *The New England J. of Medi.*, 332:259–260, 1995.

Banchereau and Steinman, "Dendritic cells and the control of immunity," *Nature*, 392:245–252, 1998.

Barnard et al., "The thiocarboxanilide nonnucleoside uc781 is a tight–binding inhibitor of hiv–1 reverse transcriptase," *Biochem.*, 36:7786–7792, 1997.

Barr, "Vaccines for HIV, HIV therapeutic vaccines: the next phase," *GMHC's Treat. Iss.*, vol. 7, No. 5, 1993.

Bender et al., "Inactivated influenza virus, when presented on dendritic cells, elicits human cd8$^+$ cytolytic t cell responses," *J. Exp. Med.*, 12:1663–1671, 1995.

Berger et al., "A new classification of HIV–1," *Nature*, 391:340, 1998.

Blauvelt et al., "Productive infection of dendtritic cells by hiv–1 and their ability to capture virus are mediated through separate pathways," *The J. of Clin. Invest.*, 100:2043–2053, 1997.

Bolognesi and Matthews, "Viral envelope fails to deliver?," *Nature*, 391:638–639, 1998.

Bombil et al., "A promising model of primary human immunization inhuman–scid mouse," *Immunobiology*, 195:360–375, 1996 (Abstract).

Borkow et al., "Chemical barriers to human immunodeficiency virus type 1 (hiv–1) infection: retrovirucidal activity of uc781, a thiocarboxanilide nonnucleoside inhibitor of hiv–1 reverse transcriptase," *J. of Virol.*, 71:3023–3030, 1997.

Borkow et al., "Inhibition of the ribonuclease H and DNA polymerase activities of hiv–1 reverse transcriptase by n–4–tert–butylbenzoyl)–2–hydroxy–1–naphthaldehyde hydrazone," *Biochemistry*, Abstract, 36(11):3179–3185, 1997.

Bryson et al., "Clearance of HIV infection in a perinatally infected infant," *The New Engl. J. of Med.*, 332:833–838, 1995.

Buckheit et al., "Efficacy, Pharmacokinetics, and in Vivo Antiviral Activity of UC781, a Highly Potent, Orally Bioavailable Nonnucleoside Reverse Transcriptase Inhibitor of HIV Type 1," *Aids Res. and Hu. Retro.*, 13:789–796, 1997.

Burr, "Of AIDS and altruism," *U.S. Nws. & W. Rpt.*, pp. 59–61, Apr. 6, 1998.

Burton and Montefiori, "The antibody response in HIV–1 infection," *Aids*, 11:S87–S98, 1997.

Cao et al., "Virology and immunologic characterization of long–term survivors of human immunodeficiency virus type 1 infection," *The New Engl. J. of Med.*, 332:201–216, 1995.

Carlson et al., "Vaccine Protection of Rhesus Macaques Against Simian Immunodeficiency Virus Infection," *AIDS Res. and Hum. Retroviruses*, 6:1239–1246, 1990.

Cella et al., "Inflammatory stimuli induce accumulation of MHC class II complexes on dendritic cells," *Nature*, 388:782–792, 1997.

Chowdry, "Photoaffinity labeling of biological systems," *Ann. Rev. Biochem.*, 48:293–325, 1979.

Clerici et al., "HIV–specific t–helper activity in seronegative health care workers exposed to contaminated blood," *JAMA*, 271:42–46, 1994.

Clotet et al., "Long–term survivors of human immunodeficiency virus type I infection," *The New England Journal of Medicine*, 332(24):1646–1647, 1995.

Cohen et al., "Characterization of the binding site for nevirapine (bi–rg–587), a nonnucleoside inhibitor of human immunodeficiency virus type–1 reverse transcriptase," *J. of Biol. Chem.*, 266:14670–14674, 1991.

Collins et al., "HIV–1 Nef protein protects infected primary cells against killing by cytotoxic T lymphocytes," *Nature*, 391:397–402, 1998.

Colonna, "Unmasking the killer's accomplice," *Nature*, 391:642–644, 1998.

Constant and Bottomly, "Induction of TH1 and TH2 CD4$^+$ T cell responses: the alternative approaches," *Annu. Rev. Immunol.*, 15:297–322, 1997.

D'Souza et al., "Neutralization of primary HIV–1 isolates by anti–envelope monoclonal antibodies," *AIDS*, 9:867–874, 1995.

DeNoon, "AIDS Therapies: new integrase inhibitor enhances other anti–HIV drugs," *AIDSWEEKLY Plus*, Nov. 23, 1998, Abstract.

Doherty and Zinkernagel, "A Biological role for the major histocompatibility antigens," *The Lancet*, 1406–1409, 1975.

Doherty and Zinkernagel, "The Specificity of the Cell Mediated Immune Defense," *The Novel Assembly at the Karolinska Institute*, Press Release Oct. 7, 1996.

Dragic et al., "HIV co–receptors: gateways to the cell," *HIV Advances in Research and Therapy*, 7(3):2–12, 1997.

Dutton et al., "T cell memory," *Annu. Rev. Immunol.*, 16:201–223, 1998.

Excler and Plotkin, "The prime–boost concept applied to HIV preventive vaccines," *Aids*, 11:S127–S137, 1997.

Ferrari, "Clade B–based HIV–1 vaccines elicit cross–clade cytotoxic T lymphocyte reactivities in uninfected volunteers," *Proc. Natl. Acad. Sci. USA*, 94:1396–1401, 1997.

Fletcher et al., "Carboxanilide derivative non–nucleoside inhibitors of hiv–1 reverse transcriptase interact with different mechanistic forms of the enzyme," *Biochem.*, 34:4346–4353, 1995.

Frankel and Young, "HIV–1: fifteen proteins and an RNA," *Annu. Rev. Biochem.*, 67:1–25, 1998.

Gibbons et al., "Thy/Liv–SCID–Hu mice implated with human intestine: an in vivo model for investigation of mucosal transmission of HIV," *Aids Res. and Hum. Retrovir.*, 13:1453–1460, 1997.

Glenn et al., "Skin immunization made possible by cholera toxin," *Nature*, 391:851, 1998.

Gotch et al., "New observations on cellular immune responses to HIV and T–cell epitopes," *Aids*, 11:S99–S107, 1997.

Graham and Wright, "Drug therapy, candidate aids vaccines," *Drug Ther.*, 333:1331–1339, 1995.

Hahn, "Viral Genes and Their Products," *Textbook of AIDs Medicine*, Chapter 3, pp. 21–43, Brother et al., eds., Williams & Wilkens, Baltimore, MD, 1994.

Hargrave et al., "Novel non–nucleoside inhibitors of hiv–1 reverse transcriptase, 1. tricyclic pyridobenzo– and dipyridodiazepinones," *J. of Med. Chem.*, 34:2231–2241, 1991.

Hong et al., "Discovery of HIB–1 integrase inhibitors by pharmacophore searching," *J. Med. Chem.*, 40:930–936, 1997, Abstract.

Huang et al., "Effect of mutations in the nucleocapsid protein (NCP7) upon PR160(GAG–POL) and trna (lys) incorporation into human immunodeficiency virus type 1," *J. of Virology*, 71(6):4378–4384, Abstract.

Huston, "The biology of the immune system," *JAMA*, 278:1804–1813, 1997.

Jawetz eds., et al., "Serologic diangosis & immunologic detection of virus infections," *Lange Medical Book*, 17th ed., Appleton & Lange, Norwalk, CT, pp. 371–380, 1987.

Jing et al., "Potassium–induced loop conformational transition of a potent anti–HIV oligonucleotide," *J. Biomol Struct. Dyn.*, 15:573–583, 1997, Abstract.

Jockusch et al., "Photo–induced inactivation of viruses: adsorption of methylene blue, thionine, and thiopyronine on Qβ bacteriophage," *Proc. Natl. Acad. Sci. USA*, 93:7446–7451, 1996.

Kim et al., "Limitation of Hu–PBL–scid mouse model in direct application to immunotoxicity assessment," *J. Pharmacol Toxicol Methods*, 37:83–89, 1997 (Abstract).

Knight and Patterson, "Bone marrow–derived dendritic cells, infection with human immunodeficiency virus, and immunopathology," *Annu. Rev. Immunol.*, 15:593–615, 1997.

Kollmann et al., "Disseminated human immunodeficiency virus 1 (hiv–1) infection in scid–hu mice after peripheral inoculation with hiv–1," *J. Exp. Med.*, 179:513–522, 1994.

LaCasse et al., "Fusion–competent vaccines: broad neutralization of primary isolates of HIV," *Science*, 283:357–362, 1999.

Lamb–Wharton et al., "Primate models of AIDS vaccine development," *Aids*, 11(suppl A):S121–S126, 1997.

Lanzavecchia, "Licence to kill," *Nature*, 393:413–414, 1998.

Letvin, "Vaccines against human immunodeficiency virus—progress and prospects," *N.E. J. of Med.*, 329:1400–1405, 1993.

Lin et al., "Photoaffinity labeling by 4–thiodideoxyuridine thriphosphate of the HIV–1 reverse transcriptase active site during synthesis," *J. Bio. Chem.*, 273:997–1002, 1998.

Loetscher et al., "CCR5 is characteristic of Th1 lymphocytes," *Nature*, 391:344–345, 1998.

Long, "Signal sequences stop killer cells," *Nature*, 391:740–741, 1998.

Luster, "Chemokines—chemotactic cytokines that mediate inflammation," *New Engl. J. of Med.*, 338:436–445, 1998.

Martinez, "Positive + Positive: Sex and the risk of reinfection," *Center for AIDS Hope & Remembrance*, 3(6):3–5, 1997.

Matthews et al., "Preliminary studies of photoinactivation of human immunodeficiency virus in blood," *Transfusion*, 31:636–641, 1991.

Mazumder et al., "Curcumin analogs with altered potencies against HIV–1 integrase as probes for biochemical mechanisms of drug action," *J. Med. Chem.*, 40:3057–3063, 1997, Abstract.

McIntosh and Burchett, "Clearance of HIV–lessons from newborns," *The New Engl. J. of Med.*, 332:883–884, 1995.

McMichael and Phillips, "Escape of human immunodeficiency virus from immune control," *Annu. Rev. Immunol.*, 15:271–296, 1997.

Meldorf and Corey, "HIV vaccines: vombination and prime–boost strategies," *HIV*, vol. 7, No. 1, pp. 24–29.

Montefiori and Moore, "Magic of the occult?," *Science*, 283:336–337, 1999.

Murphy et al., "The huPBL–SCID mouse as a means to examine human immune function in vivo," *Semin Immunol*, 8:233–241, 1996 (Abstract).

Musey et al., "Cytotoxic–T–cell responses, viral load, and disease progression in early human immunodeficiency virus type 1 infection," *The New England J. of Med.*, 337:1267–1274; 1305–1308, 1997.

Namikawa et al., "Infection of the SCID–hu mouse by HIV–1," *Science*, 242–1684–1686, 1988.

Pamer and Cresswell, "Mechanisms of MHC class I–restricted antigen processing," *Annu. Rev. Immunol.*, 16:323–358, 1998.

Pantaleo et al., "Studies in subjects with long–term nonprogressive human immunodeficiency virus infection," *N. Engl. J. Med.*, 332(4):209–216, 1995.

Pauwels et al., "Potent and selective inhibition of HIV–1 replication in vitro by a novel series of TIBO derivatives," *Letters To Nature*, 343:470–474, 1990.

Peeter et al., "Virological and polymerase chain reaction studies of HIV–1/HIV–2 dual infection in Côte d'lvoire," *Lancet*, 340:339–340, 1992.

Quinn, "Acute primary HIV infection," *JAMA*, 278:58–62, 1997.

Ren et al., "Crystal structures of HIV–1 reverse transcriptase in complex with Carboxanilide derivatives," *Biochem.*, 37:14394–14403, 1998.

Ridge et al., "A conditioned dendritic cell can be a temporal bridge between a CD4+ T–helper and a T–killer cell," *Nature*, 393:473–483, 1998.

Robinson, "L–chicoric acid, and inhibitor of human immunodeficiency virus type 1 (HIV–1) integrase, improves on the in vitro and anti–HIV–1 effect of zidovudine plus a protease inhibitor (AG1350)," *Antiviral Res.*, 39:101–111, 1998, Abstract.

Robinson, "DNA vaccines for immunodeficiency viruses," *Aids*, 11:S109–S119, 1997.

Rosenberg et al., "Vigorous HIV–1–specific cd4+ t cell responses with control of viremia," *Science*, 278:1447–1450, 1997.

Roth et al., "Synthesis and biological activity of novel nonnucleoside inhibitors of hiv–1 reverse transcriptase. 2–aryl–substituted benzimidazoles," *J. of Med. Chem.*, 40:4199–4205, 1997.

Schacker et al., "Annals of internal medicine, biological and virologic characteristics of primary HIV infection," *Ann. Intern. Med.*, 128:613–620, 1998.

Schmitz et al., "Control of viremia in simian immunodeficiency virus infection by cd8+ lymphocytes," *Science*, 283:857–860, 1999.

Schultz, "Changing paradigms for an HIV vaccine," *In: Adv. in Exper. Med. and Biol.*, 397:79–90, 1996.

Schumacher, "Immunology: accessory to murder," *Nature*, 398:26–27, 1999.

Sigal et al., "Cytotoxic T–cell immunity to virus–infected non–haematopoietic cells requires presentation of exogenous antigen," *Nature*, 398:77–80, 1999.

Smart, "The first integrase inhibitor," *GMHC Treat Issues*, 10:8–9, 1996, Abstract.

Smerdon et al., "Structure of the binding site for nonnucleoside inhibitors of the reverse transcriptase of human immunodeficiency virus type 1," *Proc. Natl. Acad. Sci.*, USA, 91:3911–3915, 1994.

Tarasiev et al., "Photochemoinactivation: a way to AIDs vaccine?,"America Online: ARIOS927, vol. 9 Issue/Part/Supplement 1, 1993 (Abstract).

Wallace et al., "Preclinical pharmacology of an anti–HIV oligonucleotide," *Int. Conf. AIDS*, 11:314, 1996, Abstract.

Watts, "Capture and processing of exogenous antigens for presentation on MHC molecules," *Annu. Rev. Immunol.*, 15:821–850, 1997.

Wu et al., "A novel dipyridodiazepinone inhibitor of HIV–1 reverse transcriptase acts through a nonsubstrate binding site," *Biochem.*, 30:2022–2026, 1991.

Yang et al., "Neutralizing antibodies against hiv determined by amplification of viral long terminal repeat sequences from cells infected in vitro by nonneutralized virions," *J. of Acq. Imm. Defic. Synd. and Hum. Retro.*, 17:27–34, 1998.

Zhao, et al., "Hydrazide–containing inhibitors of HIV–1 integrase," *J. Med. Chem.*, 40:937–941, 1997, Abstract.

Zinkernagel and Doherty, "Immunological surveillance against altered self components by sensitized T lymphocytes in lymphocytic choriomeningitis," *Nature*, 251:547–548, 1974.

Zinkernagel and Doherty, "MHC–restricted cycotoxic t cells: studies on the biological role of polymorphic major transplantation antigens determining t–cell restriction–specificity, function, and responsiveness," *Advan. In Immunol.*, New York, Academic Press, 27:51–177, 1979.

Zinkernagel and Doherty, "Restriction of in vitro T cell–mediated cytotoxicity in lymphocytic choriomeningitis within a syngeneic or semiallogeneic system," *Nature*, 248:701–702, 1974.

PCT Search Report dated Jul. 7, 1999.

Borkow et al., "Chemical barriers to Human Immunodeficiency Virus type 1 (HIV–1) infection: retrovirucidal activity of UC781, a thiocarboxanilide nonnucleoside inhibitor or HIV–1 reverse transcriptase," *Journal of Virology* 71(4):3023–3030, 1997.

Buckheit et al., "Efficacy pharmacokinetics and in vivo anti–HIV activity of the highly potent oxathiin carboxanilide analog, UC781," *Journal of Molecular Medicine* 75(7):b212–b213, 1997.

Fletcher et al., "Carboxanilide derivative non–nucleoside inhibitors of HIV–1 reverse transcriptase interact with different mechanistic forms of the enzyme," *Biochemsitry* 34(13):4346–4353, Apr. 4, 1995.

Suhadolnik et al., "Photolabeling of the enzymes of the 2–5A synthetase/RNase L/p68 kinase antiviral systems with azido probes," *Progress in Molecular and Subcellular Biology* 14:260–275, 1994.

METHOD FOR THE DEVELOPMENT OF AN HIV VACCINE

This application is a continuation-in-part application and claims priority to prior pending provisional U.S. patent application No. 60/074,646, filed on Feb. 13, 1998.

1.0 BACKGROUND OF THE INVENTION

1.1 Field of the Invention

The present invention relates generally to the fields of disease treatment and prevention. More particularly, it concerns HIV particles with inactivated reverse transcriptase and the use of such particles to elicit an effective immunological response to HIV. This immune response will provide protection from an HIV challenge and/or will assist the HIV-infected individual in controlling the replication of the virus.

1.2. Description of Related Art

1.2.1 Human Immunodeficiency Virus

Human Immunodeficiency Virus-1 (HIV-1) infection has been reported throughout the world in both developed and developing countries. HIV-2 infection is found predominately in West Africa, Portugal, and Brazil. It is estimated that as of 1990 there were between 800,000 and 1.3 million individuals in the United States that were infected with HIV. An important obstacle to developing a vaccine against HIV is that the mechanism of immunity to HIV infection is ill-understood. Not all of those infected individuals will develop acquired immunodeficiency syndrome (AIDS). Indeed recent reports have suggested that there may be certain individuals that are resistant to HIV-1 infection.

The HIV viruses are members of the Retroviridae family and, more particularly, are classified within the Lentivirinae subfamily. Like nearly all other viruses, the replication cycles of members of the Retroviridae family, commonly known as the retroviruses, include attachment to specific cell receptors, entry into cells, synthesis of proteins and nucleic acids, assembly of progeny virus particles (virions), and release of progeny viruses from the cells. A unique aspect of retrovirus replication is the conversion of the single-stranded RNA genome into a double-stranded DNA molecule that must integrate into the genome of the host cell prior to the synthesis of viral proteins and nucleic acids.

Retrovirus virions are enveloped and contain two copies of the genome. The conversion of the genomic RNA into DNA is provided by the viral protein reverse transcriptase (RT). This protein is bound to the RNA genome within the virion, and its enzymatic conversion of the genome to DNA is believed to take place after viral entry into the host cell. However, recent evidence suggests that the conversion process may initiate in the virion particles themselves, known as endogenous reverse transcription (ERT), and that ERT may be important in increasing the infectivity of the virus in sexual transmission (Zhang et al., 1993, 1996).

Because of the requirement for reverse transcription in the viral replication cycle, compounds that interfere with RT activity have been utilized as anti-HIV therapeutic agents. Many of these compounds, including 3'-azido-2', 3'-dideoxythymidine (AZT), are nucleoside analogs that, upon activation by host cell kinases, are competitive inhibitors of reverse transcriptase (Furman et al., 1986). Other anti-RT compounds are nonnucleoside inhibitors (NNI), hydrophobic compounds that do not require cellular modification for antiviral activity. Examples of such compounds include nevirapine (Grob et al., 1992; Merluzzi et al., 1990), the pyridinones (Carroll et al., 1993; Goldman et al., 1991), and the carboxanilides (Bader et al., 1991; Balzarini et al., 1995, 1996). The nevirapine analog 9-azido-5,6-dihydro-11-ethyl-6-methyl-11H-pyrido[2,3-b][1,5]benzodiazepin-5-one (9-AN) and the carboxanilide analog N-[4-chloro-3-(3-methyl-2-butenyloxy)phenyl]-2-methyl-3-furanocarbothiamide (UC781™) have been shown to be potent inhibitors of RT. In respect of the 9-AN, the exposure of a mixture of this compound and RT to UV-irradiation has been particularly effective in inhibiting RT. From the series of carboxanilides compounds, UC781™ has been found to be particularly effective (Barnard et al., 1997). The addition of a photoreactive label to UC781™ should increase further its ability to inactivate HIV RT, when a mixture of UC781™ and RT is exposed to UV-irradiation. The irradiation of a mixture of a photolabeled NNI of RT and RT is a type of photoinactivation.

The binding affinity and inhibitory effect of UC781™ is so high that the compound was able to eliminate HIV infectivity following short exposure of the isolated virus to UC781™ without the need for photoinactivation (Borkow et al., 1997). Further, this compound was shown to inhibit ERT in HIV virions and, when provided to HIV infected cells, caused the production of noninfectious nascent virus (Borkow et al, 1997). Therefore, it appears that UC781™ is a particularly powerful inactivator of HIV. Although UC781™ has been proposed for use in retrovirucidal formulations (Borkow et al., 1997), use as a photoinactivator of HIV for the purpose of producing a vaccine is absent from the prior art.

1.2.2 Immune Response to HIV

The immune response to HIV is composed of an initial cell mediated immune response followed by the subsequent development of neutralizing antibodies. Within weeks of infection, virus titers in the blood fall coincident with the induction of anti-HIV cellular and humoral immune responses. The fall in viremia correlates well with the appearance of anti-HIV major histocompatibility complex (MHC) class I-restricted CD8$^+$ cytotoxic T cells (Haynes et al., 1996). Recent evidence has shown a strong correlation of anti-HIV CD4$^+$ T cell responses and reduced viral loads (Rosenberg et al, 1997). Therefore, the presentation of HIV antigens in the context of MHC class II molecules to CD4$^+$ T cells may be the key aspect of the control of the HIV infection.

Rosenberg et. al. (1997) suggest that in HIV-1 infection, HIV-specific CD4$^+$ cells may be selectively eliminated. This may be due to the activation of these cells during high-level viremia, increasing their susceptibility to infection (Weissman et al., 1996; Stanley et al., 1996), or may be due to activation induced cell death during primary infection (Abbas, 1996). Nonetheless, increasing the virus-specific CD4$^+$ T cell response without infecting, or destroying, the responding cells may be an effective means of controlling viral loads. Therefore, some existing HIV vaccines may be ineffective because they do not provide presentation of HIV peptides in the context of MHC class II by antigen presenting cells.

1.2.3 HIV Vaccines

Historically, viral vaccines have been enormously successful in the prevention of infection by a particular virus. Therefore, when HIV was first isolated, there was a great amount of optimism that an HIV vaccine would be developed quickly. However, this optimism quickly faded because a number of unforeseen problems emerged. A discussion of the problems that an HIV vaccine must overcome is provided within Stott and Schild (1996) and is incorporated herein by reference.

First, HIV is a retrovirus, thus, during its growth cycle, proviral DNA is integrated in the host genome. In this form the virus is effectively protected from the immune response of the host and this feature of the virus suggests that effective vaccination must ideally prevent the initial virus-cell interaction following transmission. Few, if any, of the currently available successful viral vaccines against other infections achieve this level of protection. Secondly, HIV specifically targets and destroys T-helper lymphocytes, which form an essential component of the immune response. Thirdly, the virus is capable of extremely rapid antigenic variation which permits escape of the virus from immune responses. Fourthly, the majority of infections are acquired sexually via the genital or rectal mucosae, and infections of this route are generally considered difficult to prevent by vaccination. Finally, infection may be transmitted by virus-infected cells in which the proviral DNA is integrated and viral antigens are not expressed. Such a cell would not be recognized by immune responses to viral proteins and would therefore pass undetected. Few data are available to indicate how significant this mode of transmission is in the overall epidemiology of HIV-1. Nevertheless, it represents a potential route and one which some authorities believe cannot be blocked by vaccination (Sabin, 1992).

Types of HIV vaccines include inactivated virus vaccines, live attenuated virus vaccines, virus subunit vaccines, synthetic particle vaccines, and naked DNA vaccines and are reviewed in Stott and Schild (1996), Schultz (1996), and Johnston (1997). Several of these vaccines are already in human trials.

The first evidence that vaccination against immunodeficiency viruses was feasible came from early experiments using simple inactivated virus prevented the onset of disease when vaccinated animals were subsequently challenged (Desrosiers et al., 1989; Sutjipto et al., 1990). These results were confirmed and extended by Murphey-Corb et al. (1989) who showed that most animals immunized with formalin-inactivated virus were protected against infection with SIV. Similar results were subsequently obtained by several laboratories using virus-infected cells (Stott et al., 1990) or partially purified virus, inactivated by aldehydes (Putkonen et al., 1991, 1992; Johnson et al., 1992a; Le Grand et al., 1992), β-propiolactone (Stott et al., 1990) detergent (Osterhaus et al., 1992) or psoralin and UV light (Carlson et al., 1990). Several different isolates of SIV or infectious molecular clones derived from them were used to prepare the vaccine and challenge viruses. A wide variety of adjuvants were also employed. On every occasion vaccinated macaques were protected against infection by intravenous challenge of between 10–50 $MID_{50}$ (50% monkey infectious doses). Infections virus could not be recovered from the blood or tissues of the protected animals even when they were followed for prolonged periods of over 1 year. Even more impressive was the failure to detect proviral DNA in the lymphocytes of protected animals, indicating that there had been no integration of the challenge virus (Stott et al., 1990; Johnson et al., 1992a). It was thus clear that inactivated virus vaccines induced a powerful protective response in macaques. Unfortunately, the protection induced by inactivated SIV in macaques was not reproduced in chimpanzees vaccinated with inactivated HIV and challenged with HIV-1 (Warren and Doltshahi, 1993).

1.2.4 Photoinactivation of HIV

Methods of photoinactivation of HIV are known in the art and have been the subject of at least three patents. U.S. Pat. No. 5,041,078 describes the use of sapphyrins in the photodynamic inactivation of viruses, including HIV. U.S. Pat. Nos. 5,516,629 and 5,593,823 describe the use of psoralens and ultra violet light to inactivate HIV. U.S. Pat. No. 5,516,629 is incorporated herein by reference. Psoralens are naturally occurring compounds which have been used therapeutically for millennia in Asia and Africa. A psoralen binds to nucleic acid double helices by intercalation between base pairs. Upon absorption of UVA photons, the psoralen excited state has been shown to react with a thymine or uracil double bond and covalently attach to both strands of a nucleic acid helix. The crosslinking reaction is specific for a thymine (DNA) or uracil (RNA) base and will proceed only if the psoralen is intercalated in a site containing thymine or uracil. The initial photoadduct can absorb a second UVA photon and react with a second thymine or uracil on the opposing strand of the double helix to crosslink the two strands of the double helix.

Lethal damage to a cell or virus occurs when a psoralen intercalated into a nucleic acid duplex in sites containing two thymines (or uracils) on opposing strands sequentially absorb 2 UVA photons. This is an inefficient process because two low probability events are required, the localization of the psoralen into sites with two thymines (or uracils) present and its sequential absorption of 2 UVA photons.

Attempts to inactivate viruses using photosensitizers and light have also been developed using some non-psoralen photosensitizers. The photosensitizers that have been employed are typically dyes. Examples include dihematoporphyrin ether (DHE), Merocyanine 540 (MC540) and methylene blue.

Carlson et al. (1990) has shown that a psoralen-inactivated whole SIV (the Simian counterpart of HIV) vaccine can protect against low challenge doses of SIV and prevent early death in those monkeys that do become infected, suggesting that inactivated HIV may be an effective vaccine in humans. However, because photoinactivation using psoralens is dependent on two rare events, a more efficient method of inactivation is preferable to decrease the likelihood of live virus within a sample. Furthermore, these methods alter the antigenic conformation of HIV affecting the production of an effective immunological response.

1.3 Deficiencies in the Prior Art

Due to previous successes in preventing viral diseases using subunit, live-attenuated viral, and inactivated viral vaccines, the scientific community was initially optimistic that a vaccine would be developed to prevent the spread of HIV. However, early optimism soon diminished because of repeated failures in the development of an effective vaccine.

Subunit vaccines, although extremely safe, are limited in the breadth of antigens that are presented to the immune system because only one or a few of the viral proteins are utilized in the vaccine. This may limit the likelihood of cross protection between clades of HIV. Also, the production of subunit vaccines requires the molecular manipulation of the viral proteins into cloning or expression vectors, perhaps leading to increased production time and costs.

Live-attenuated HIV vaccines may also require molecular manipulations in their production, although spontaneous attenuated viruses may occur naturally. Attenuated HIV vaccines have included deletions in the nef region of the virus. Mutant-nef SIV vaccines showed initial promise in primates, however, it was quickly shown that these vaccines were capable of causing disease in newborn animals. Furthermore, recent evidence suggests that these vaccines are capable of causing full-blown AIDS in adult monkeys (Cohen, 1997). Therefore, the lack of an efficient understanding of HIV and its pathogenesis makes the use of attenuated viruses a risky endeavor.

Inactivated viral vaccines provide a larger compliment of antigens that are presented to the immune system, and, therefore, provide a greater amount of protection from HIV and is more likely to provide protection across HIV clades. Furthermore, the inactivated viral vaccines do not require molecular manipulation of HIV and can be made to essentially any strain. Because inactivation of the virus is readily shown in in vitro and animal models, the inactivated HIV vaccines are able to be tested in a timely manner to determine the effectiveness of inactivation. Attenuated viruses may take years to determine the effectiveness of the vaccine.

To be safe to administer to humans, efficient methods of inactivation of HIV are required for vaccine production. Methods known for the inactivation include the use of aldehydes, β-propiolactone, psoralin and UV light, and others including detergents. Many of these methods alter the conformation of the virus thereby altering the specificity of the immune response to the virus. Photoinactivation of HIV using psoralin and UV light does not alter the conformation of the virus, but it is an inefficient method of inactivation. Therefore, more efficient methods of inactivation that do not affect the conformation of the virus would be ideal for use in the production of an HIV vaccine.

2.0 SUMMARY

The prior art is devoid of HIV vaccines created using an efficient method of inactivating HIV without causing deformation of the viral particle. The vaccine of the present invention is produced using efficient methods of inactivation that do not alter the conformation of the virus to the same extent as other inactivation methods. Therefore, the vaccine of the present invention mimics infectious HIV particles but does not cause infection (i e., establishment of a perpetuation of HIV within the recipient host due to incorporation of HIV into the genome of cells within that host).

The use of an azido dipyrodiazepinona and an azido thiocarboxanilide (azido UC781™), azido-labeled compounds shown to bind and inactivate RT, permits the generation of non-infectious particles of HIV by inactivating the HIV RT upon exposure of infectious particles to either compound followed by irradiation with ultraviolet light. The effective inactivation of HIV RT by the methods described herein allows the production of non-infectious particles of HIV. These non-infectious particles of HIV have the capacity of eliciting an effective cell mediated and antibody mediated immune response which is protective against infection by HIV. The inactivated HIV particles of the present invention preserve the antigenic composition of infectious wild-type HIV particles and thereby facilitate the dendritic cell-mediated processing and presentation of HIV particle-derived antigens to T cells.

The application of this methodology to different strains of HIV may allow the production of a polyvalent vaccine (NIIPAV or NON-Infectious Immunogenic Polyvalent AIDS Vaccine). The inactivated HIV particles of the present invention upon binding to CD4 receptors will expose epitopes which may elicit broad immunogenic responses capable of inhibiting the infectivity of diverse types of HIV from different clades. Thus the exposure of the immune system to a single type of inactivated particle of the present invention may protect against infection by multiple types of HIV.

One aspect of the present invention is a composition comprising an HIV particle in which the RT is inactivated. The composition may further comprise a pharmaceutically-acceptable excipient. The present invention contemplates that the HIV particle may be any type, subtype or isotype of HIV. In a preferred embodiment, the HIV particle is a wild type HIV particle. In one embodiment the HIV particle is HIV 1. The HIV 1 particle may be Group M or Group O. In different embodiments the Group M HIV 1 may be clade A, clade B, clade C, clade D, clade E, clade F, clade G, clade H, or clade I. In a preferred embodiment of the invention, the Group M particle is a clade B particle.

In one embodiment the RT is inactivated by one or more compounds that binds the RT and then irradiating bound RT with UV light. In a preferred embodiment the UV light is that emitted by a GE 275 W sun lamp. However, it is contemplated that any light that causes the reaction of the compound with RT may be used. In one embodiment of the compound that binds to RT is an azido labeled compound. Essentially any azido-labeled compound that binds to HIV RT and can penetrate the HIV particle so as to associate with RT may be used. In a preferred embodiments the azido-labeled compound is azido dipyrodiazepinona or azido-UC781™. In other embodiments the azido-labeled compound is the azido derivative of 9-AN, UC38, UC84, UC10, UC82, UC040, HBY 097, calanolide A, or U-88204E. In one embodiment the inactivation of RT comprises contacting said HIV particle with an effective amount of the azido labeled compound.

Another aspect of the present invention is a method of invoking an immune response in an animal by administering a composition comprising a pharmaceutically-acceptable excipient and an HIV particle in which the RT is inactivated. The immune response may be a humoral response, a cellular response or both a humoral and cellular response. The cellular response may be a CD8+ T cell response, a CD4+ T cell, or both a CD8+ T cell and a CD4+ T cell response.

The animal in which the immune response is invoked may be a mammal. In preferred embodiments the mammal may be a human, a PBL-SCID mouse, or a SCID-hu mouse. The animal in which the immune response is invoked may be either HIV positive or HIV negative.

Another aspect of the present invention is a method of delaying the onset of AIDS in an animal exposed to infectious HIV by administering to the animal an inoculation of a pharmaceutically acceptable excipient and an HIV particle in which the RT is inactivated. The animal may be a mammal and in preferred embodiments the mammal is a human, a PBL-SCID mouse, or a SCID-hu mouse. The animal may be either HIV negative or HIV positive at the time of the administration of the inoculation.

Another aspect of the present invention is a method of making an HIV particle containing an inactivated RT comprising contacting a compound capable of inactivating RT with an HIV particle such that the compound binds to the RT and then irradiating the HIV particle. In one embodiment the HIV particle is HIV 1. The HIV 1 particle may be Group M or Group O. In different embodiments the Group M HIV 1 may be clade A, clade B, clade C, clade D, clade E, clade F, clade G, clade H, or clade I. In a preferred embodiment of the invention, the Group M particle is a clade B particle.

In one embodiment of the compound capable of inactivating RT is an azido labeled compound. Essentially any azido-labeled compound that binds to HIV RT and can penetrate the HIV particle so as to associate with RT may be used. In preferred embodiments the azido-labeled compound is azido dipyrodiazepinona or azido-UC781™. In other embodiments the azido-labeled compound is the azido derivative of 9-AN, UC38, UC84, UC10, UC82, UC040, HBY 097, calanolide A, or U-88204E.

Another aspect of the present invention is a method of preparing a composition comprising making an HIV particle containing an inactivated RT by contacting a compound capable of inactivating RT with an HIV particle such that the compound binds to the RT, irradiating the HIV particle, and then combining the HIV particle with the inactivated RT with a pharmaceutically acceptable excipient.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Simplified phylogenetic tree of HIV-1. Group M denotes the major of HIV-1; group O refers to outliers or outgroup. Sequence data from the env gene C2V3 region of selective isolates of subtypes A through H were compared to construct the phylogenetic tree. A ninth subtype, I, has been reported recently but is not shown because the isolate was characterized using a different segment of the env gene. The horizontal branch lengths represent approximate relative genetic distances. (From Hu D J, Dondero T J, Rayfield M A, et al., The emerging genetic diversity of HIV: The importance of global surveillance for diagnostics, research, and prevention. JAMA 275:210, 1996.).

4.0 DESCRIPTION OF ILLUSTRATIVE EMBODIMENTS

The present invention relates to a vaccine comprising RT-inactivated HIV for the purpose of eliciting a protective immune response in an animal. The present invention employs methods of inactivating RT. Further, the use of these inactivation methods for the purpose of producing a vaccine is novel.

There are well described methods for the isolation and culture of HIV. What is important to keep present in regard to the objectives of this invention is the fact that, using a methodology that inactivates the HIV reverse transcriptase, non-infectious particles of HIV are obtained which are capable of eliciting an effectively protective immune response. Thus, although it makes sense to describe the method using specific strains of HIV and specific types of cells for the culture and testing of the lack of infectiousness of the generated particles, it should be kept in mind that this method may apply to different strains of HIV, including laboratory and primary isolates.

In fact, given the geographic diversity of distribution of different strains of HIV, it makes sense to utilize many strains of HIV with this methodology. The combined use of different strains of inactivated particles of HIV is what will confer to this potential vaccine preparation its polyvalent characteristics. Thus, in describing the method to generate the vaccine particles and its testing for safety and efficacy, the inventor sought to establish the general principles of the methodology for its subsequent application. It should be understood that the inactivator of the HIV reverse transcriptase to be used in the initial study can be compared to other inactivators in parallel studies and thus allow for the selection of the most effective one.

It of importance to note that the methodology of the present invention is applicable to any retrovirus which may be associated with any animal or human disease as a method for development of an effective preventive vaccine. Thus, the present invention has a broader applicability than the exemplified HIV vaccine.

4.1 Human Immunodeficiency Virus

The genetic diversity of HIV is due to the extremely high replication rate in infected individuals, the high rate of mutation caused by the error-prone reverse transcriptase, the substantial viral load, and selection within infected individuals (Doolittle, 1989; Ho et al., 1995; Piatek et al., 1993). Diversity is so great that the presence of closely related but not identical strains of HIV, known as quasispecies, commonly appear in a single, infected individual. The quasispecies may diverge increasingly over time and changes tend to be within the env gene, particularly the V3 region (Hwang et al., 1992). Although changes also may occur in the gag, pol, and accessory genes, these differences tend to be less substantial.

When significant changes accumulate and are seen in a large group of individuals, the strain is commonly considered a new family or new clade of HIV. Phylogenetic studies of HIV have shown that there are two major families of HIV, HIV-1 and HIV-2. Within the HIV-1 family there are two major antigenic groups, known as Group M (major) and Group O (outlier). Each of these two groups has in turn different subtypes or clades which, when analyzed, lead to the conclusion that both probably originated from two primordial viral ancestors. The group M is responsible for most of the HIV infections throughout the world and the group O is rarely found and confined to Cameroon, Gabon and France. There are at least nine subtypes or clades in the group M and of these, the subtype B is prevalent in the Western Hemisphere, while the subtypes A, C and D are in Africa. In Asia, the most frequently found subtypes are E, C and B, with the subtype E having a high prevalence in Southeast Asia. In India the prevalent subtype is C. A phylogenetic tree based on the sequence data from the env gene C2V2 region of selected isolates of the different subtypes is shown in FIG. 1. The geographic distribution of the different clades is shown in Table 1 (Hardy, 1996).

TABLE 1

Worldwide Geographic Distribution of HIV-1 Subtypes and HIV-2

| | HIV-1 Subtypes | | | | | | | | | | HIV-2 |
|---|---|---|---|---|---|---|---|---|---|---|---|
| | Group M | | | | | | | | | | |
| | A | B | C | D | E | F | G | H | I | O | HIV-2 |
| Africa | + | + | + | + | + | + | + | + | | + | + |
| Middle East | | | | | | | | | + | | |
| Europe | + | + | + | + | | + | + | + | | + | + |
| Asia | | + | + | | + | | | | | | |
| India | + | + | + | | | | | | | | + |
| Australia | | + | | | | | | | | | |
| North America | | + | | | | | | | | | + |
| South America | | + | + | | + | | | | | | |

A vaccine comprising one clade may provide for the protection of infection by one or more other clades. A very important concept when confronting what appears to be the very difficult challenge of antigenic variation is the understanding of the concept of critical antigenic consistency. By critical antigenic consistency it is meant that there is a critical number of epitopes which are found consistently in HIV. Although it is recognized that there are significant antigenic changes in the configuration of the envelope proteins, generally, the internal proteins have less sequence variation. It has been recently demonstrated that epitopes, of critical immunologic importance, are exposed or created as HIV begins to fuse with cell membranes. The fusion process results in a conformational change of envelope glycoproteins leading to the exposure of previously occult epitopes or the de novo formation of epitopes. The recent use of these fusion exposed epitopes has led to the preparation of antibodies which are capable of inhibiting the infectivity of multiple primary HIV isolates, including multiple genetic subtypes (Montefiori and Moore, 1999; LaCasse et al., 1999). The broad immunological protection elicited by the fusion exposed epitopes may explain the observation that people infected with HIV-1 virtually never have more than one subtype of virus.

These significant recent results indicate that once the immune system is exposed to HIV without integration of HIV in the genetic machinery of the host, the immune response will be effective and of a broad base. The non-infectious HIV particles of the part invention mimic the antigenic structure and composition of natural infectious HIV particles. Thus, these non-infectious particles will penetrate susceptible cells, including cells of the immune system responsible for the generation of the immune response, in the identical fashion as infectious particles, that is by receptor/co-receptor binding and fusion. The receptior-mediated entry of the vaccine into cells will result in exposure of the superior immunogenic epitopes and thereby facilitate the creation of a broad immunogenic response.

In addition to the recently described fusion exposed epitopes, the consistent regions of the env, gag, and pol together can lead to a critical mass of antigens responsible for the production of an effective immunological response to HIV and, which in fact, are present in nearly all types and subtypes of HIV. Thus, although it will be wise to use different wild types to create non-infectious particles and create a polyvalent vaccine, it is also possible that exposure of the immune system to a single type of inactivated HIV particle will be enough to generate a broad immune response.

The antigenic configuration of HIV is of the utmost importance since it is known that conformational epitopes can be located in variable regions of the HIV particle and can not be predicted from the analysis of the linear sequences of these regions. Therefore, it is of great importance that, in eliciting an effective protective immune response against HIV, the immune system is presented correct antigenic conformations.

Substantial evidence indicates that dendritic cells ("DC") present in epithelial tissues (e.g., Langerhans cells) are the initial cells infected with HIV after mucosal exposure to the virus (Cameron et al., 1996; Knight, 1996). The bone marrow-derived DC are a class of antigen-presenting cells ("APC") that survey epithelial tissues for anitgens and are efficient stimulators of both B and T lymphocytes. Unlike B cells, T cells cannot directly recognize antigens and require that antigens be processed and presented by APCs (Banchereau and Steinman, 1998). Intracellular processing of antigens to peptide fragments results in binding to MHC class I molecules and a CD8+ cytotoxic T cell response. In contrast, antigens that enter DC by the endocytic pathway generally bind to MHC class II molecules the elicitation of a CD4+ helper T cell response (Banchereau and Steinman, 1998).

Inactivated HIV viral particles will be processed and presented by DC as long as the inactivated HIV particles are preserved in its antigenic composition and can access the cytoplasm of the dendritic cells. Both of these conditions are met by the present invention. That is, the inactivated particles have a preserved envelope structure and thus will access the cytoplasm of the dendritic cell by a process of micropinocytosis or mannose-receptor mediated uptake. DC that have been exposed to the inactivated HIV particles will migrate to the lymph nodes where they will interact with T-cells presenting MHC-antigens complexes to both memory and naive T-cells (see Banchereau and Steinman, 1998; Bender et al., 1995). This process will lead to the development of an effective anti-HIV MHC-I restricted CD8+ T-cell response. Cytotoxic CD8+ T cells are recognized as having an important role in controlling HIV invention (Musey et al., 1997; Oldstone, 1997).

Dendritic cells also have CD4/HIV co-receptors and thus can be infected by HIV. This infectious process is independent of the capture and processing of HIV for antigenic presentation and initiation of the MHC class I restricted immunological response (Blauvelt et al., 1997). But since the inactivated particles are non-infections, the process of penetration through a receptor mechanism will allow the production of a MHC-II restricted response. Thus DC cells will activate and expand CD4+ T helper cells, which in turn will induce B cell growth and antibody production. This MHC class II response will thereby complement the MHC class I restricted immune response by establishing an effective cytotoxic and humoral response as well as an effective immunological memory.

The inventor contemplates that the present invention may be comprised of inactivated viruses from one or more clades of HIV. In preferred embodiments, the vaccine may be comprised of inactivated viruses of the clade or clades which with the individual is most likely to come in contact. The data of Table I may be used as a guide to determine which clades are prevalent in different geographical areas.

Because the present invention may be produced cheaply and rapidly, an individual may be vaccinated with inactivated virus or even inactivated HIV infected cells from the individual most likely to pass or have passed the virus to the individual. For example, an HIV-negative person may be vaccinated with inactivated HIV or inactivated HIV-infected cells from an HIV-positive individual with which the HIV-negative individual plans to or has already come in sexual contact. An example of such a HIV-negative individual could be someone married to a hemophiliac that is HIV-positive. Additionally, these "personal" vaccines may have the benefit of also having cellular (nonviral) surface proteins from the individual passing the virus. The immune response to cellular surface proteins incorporated into the virus particles, which include MHC antigens, have been shown to confer protection from future challenges from viruses grown in the same cell line (Stott et al., 1991).

4.2 Photoinactivation of Reverse Transcriptase

A number of non-nucleoside inhibitors of HIV reverse transcriptase have been described and include neviprine and its analogs, the pyridobenzo- and dipyridodiazepinones, the pyridones, the quinoxalines, and the carboxanilides. Specific compounds include 9-AN, UC781™, UC38, UC84, UC10, UC82, UC040, HBY 097, calanolide A, U-88204E, and many others (Barnard et al., 1997; Esnouf et al., 1997; Buckheit et al., 1997; Kleim et al., 1997; Currens et al., 1996; Althaus et al., 1993). These compounds may be converted to azido photoaffinity labels and utilized for the inactivation of HIV particles using methods described herein. The inventor contemplates that essentially any compound that binds and inhibits HIV RT, is able to penetrate the viral particle and associate with RT, and does not cause significant alterations in the conformation of the virus particle may be used to produce an RT-inactivated virus for the purpose of eliciting a protective immune response in an individual. Furthermore, the inventor contemplates that the exposure of the photaffinity label-treated particles to light radiation to irreversibly inactivate the RT may comprise of light of a variety of wavelengths. Although UV light, particularly that emitted by a GE 275 W sun lamp, is preferred, any exposure to light that causes the reaction of the azido compound with RT is contemplated to be of utility in the production of the compositions of the present invention.

4.3 Vaccine Preparation

The inactivation of the virus by photoinactivation of RT provides noninfectious, immunogenic particles that are essential identical in conformation and composition as infectious particles. Therefore, the inventor contemplates that particles inactivated in this method are ideal for use as a potential vaccine against HIV diseases including AIDS and AIDS-related conditions. Thus the present invention provides an immunogenic composition that may be used as a vaccine against HIV infection and its consequences, including AIDS and AIDS-related conditions. The immunogenic compositions elicit an immune response which produces cellular and humoral immune responses that are antiviral. If a vaccinated person is challenged by HIV, T cells of the cellular response will eliminate infected cells and antibodies of the humoral response will inactivate the virus by binding to its surface.

Vaccines may be injectable liquid solutions or emulsions. The RT-inactivated HIV particles may be mixed with pharmaceutically-acceptable excipients which are compatible with the inactivated virus particles. By compatible it is meant that the phamaceutically-acceptable excipients will not alter the conformational characteristics of the viral particle. Excipients may include water, saline, dextrose, glycerol, ethanol, or combinations thereof. The vaccine may further contain auxiliary substances, such as wetting or emulsifying agents, buffering agents, or adjuvants to enhance the effectiveness of the vaccines. Adjuvants may be mineral salts (e.g., $AlK(SO_4)_2$, $AlNa(SO_4)_2$, $AlNH_4(SO_4)$, silica, alum, $Al(OH)_3$, $Ca_3(PO_4)_2$, kaolin, or carbon), polynucleotides (e.g., poly IC or poly AU acids), and certain natural substances (e.g., wax D from *Mycobacterium tuberculosis,* substances found in *Corynebacterium parvum, Bordetella pertussis,* or members of the genus Brucella) (PCT Application No. 91/09603). Aluminum hydroxide or phosphate (alum) are commonly used at 0.05 to 0.1 percent solution in phosphate buffered saline. Other adjuvant compounds include QS21 or incomplete Freunds adjuvant.

Vaccines may be administered parenterally, by injection subcutaneously or intramuscularly, or the vaccines may be formulated and delivered to evoke an immune response at the mucosal surfaces. The immunogenic composition may be administered to a mucosal surface by the nasal, oral, vaginal, or anal routes. The inventor contemplates that the administration of the immunogenic compound to a mucosal surface that is most likely to be challenged by HIV, such as the anal, vaginal, or oral mucosa, is preferred. For vaginal or anal delivery, suppositories may be used. Suppositories may comprise binders and carriers such as polyalkalene glycols or triglycerides. Oral formulations may be in the form of pills, capsules, suspensions, tablets, or powders and include pharmaceutical grades of saccharine, cellulose or magnesium carbonate. These compositions may contain 10% to 95% of the RT-inactivated viral particles.

Preferably the vaccines are administered in a manner and amount as to be therapeutically effective. That is to say that the vaccine should be administered in such a way as to elicit an immune response to the RT-inactivated viral particles. Suitable doses required to be administered are readily discernible by those of skill in the art. Suitable methodologies for the initial administration and booster doses, if necessary, maybe variable also. The dosage of the vaccine may depend on the route of administration and may vary according to the size of the host. One of skill in the art may obtain details regarding the practice and use of the present invention in the American Foundation for AIDS Research's HIV Experimental Vaccine Directory, Vol 1, No. 2, June 1998, which is hereby incorporated by reference in its entirety.

Although the immunogenic compositions of the present invention may be administered to individuals that are not infected with HIV, HIV-negative, they also may be administered to individuals who are infected with the virus in an effort to alter the immune response to the virus. The alteration may be a stimulation of anti-HIV $CD4^+$ or $CD8^+$ T cells, an increase in antibody production, or in respect to the type of response to the virus (i.e., $T_H1$ vs. $T_H2$). Nonetheless, this alteration if effective will decrease the mortality and morbidity associated with the HIV infection. In other words, the immunogenic compound may decrease the severity of the disease and increase the life of the patient.

4.4 Pharmaceutical Compositions

Where clinical application of a vaccine according to the present invention is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the inactivated virus, dissolved or dispersed in a pharmaceutically acceptable carrier or aqueous medium. Such compositions also are referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The inactivated viruses and inactivated virus-producing cells of the present invention may include classic pharmaceutical preparations. Administration of pharmaceutical compositions according to the present invention will be via any common route so long as the target tissue is available via that route. This includes oral, nasal, buccal, rectal, vaginal or topical. Alternatively, administration will be by orthotopic, intradermal, intraocular, subcutaneous, intramuscular, intraperitoneal or intravenous injection. Such compositions would normally be administered as pharmaceutically acceptable compositions that include physiologically acceptable carriers, buffers or other excipients.

The pharmaceutical compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well known parameters.

The compositions of the present invention may comprise a supplement of one or more compounds capable of preventing the replication of HIV, including the compound utilized to inactivate the virus. These compounds may include, but are not limited to, nucleoside analog inhibitors of HIV RT (e.g., AZT), non-nucleoside inhibitors of HIV-RT (e.g., UC781™), or HIV protease inhibitors.

4.5 Safety of the Vaccine

The safety of the vaccine particles may be demonstrated by their inability to produce infection in susceptible cells regardless of the amount of particles used as inoculum. Controlled studies may conducted exposing susceptible cells to increased concentrations of these particles. Particles which have their RT inactivated will fail to infect susceptible cells, while the control studies will maintain the capacity to produce infection in the susceptible cells. The same methodology that was used to generate the viral particles may be used to test the inactivation of the virus particles of the present invention. For monitoring infectivity in both the non-infectious particles and the controls, the inventor contemplates the monitoring of production of RT and p24 antigen in the culture supernatants. In a preferred embodiment, supernatants are tested for the presence of virus particles by the sensitive method of heminested polymerase chain reaction (HNPCR) amplification of the 5' LTR sequences (LTR-HNPCR). This test will confirm the absence of infectivity of the vaccine particles since there is an excellent correlation between a negative infectivity test and a negative LTR-HNPCR (Yang et al., 1998).

The safety of the particles can also be evaluated in vivo by inoculation of the animal models discussed infra in section 4.6. The lack of infectivity of the inactivated particles can be determined by repeated high dose inoculation of animals such as PBL-SCID mice, SCID-hu mice, or non-human primates.

As a way of creating an additional safety mechanism for this vaccine, HIV integrase, an enzyme required for viral integration, can be inactivated. It is important to clarify that since the reverse transcritpase of the viral particle is inactivated there will be no replication of the virus. The inactivated of HIV integrase would be an added safety feature. Without a functional integrase there is no possibility for the integration of HIV into the genetic material of the cell further ensuring the safety of the vaccine. The mechanism for integrase inactivation will be one of selective photolabeling using a (as azido group) bound to any of several compounds that are known to bind to HIV-integrase. Among these compounds are: anti-integrase oilgonucelotides, L-chicoric acid, as well as a large number hydrazine derivative inhibitors.

4.6 Administration

Although it is important to consider different routes of administration, the intramuscular route will be the route of choice. Other routes include: 1) intranasal; 2) intrarectal; 3) intravaginal; 4) oral and 4) subcutaneous. The dose to be used will be measured in viral particles and it will have a range from the administration of 1 particle to $10^{20}$ particles. It is anticipated that the optimal range of dosing will be between $10^4$ particles and $10^8$ particles. Thus lower dose ranges may include doses of about 10, $10^2$, or $10^3$ particles. Optimal dose ranges may include doses of about $10^4$, $10^5$, $10^6$, $10^7$, or $10^8$ particles. Higher dose ranges may include doses of about $10^{10}$, $10^{12}$, $10^{14}$, $10^{16}$, $10^{18}$ or $10^{20}$ particles. The effective dosage may vary depending on the method of administration.

For each dose to be tested, the schedule may consist of administration of a dose on days 0, 30, 60, and a booster dose at 180 days. Alternatively doses may be given weekly, every two weeks, or monthly for periods of one, two, three, four, five or six months. Doses may also be given every two months for a similar time. Periodic booster shots at intervals of 1–5 years may be desirable to maintain protective levels of immunity. Other administration schedules may be used and the invention contemplates any administration schedule that results in an effective vaccination.

In addition to monitoring for clinical safety, efficacy will be assessed by measuring the cellular and humoral immune response to HIV. Subjects will be followed for a period of two or more years from day 0 (date of first inoculation).

4.7 Animal Models

A number of different animal model systems for HIV infection have been employed (Kindt et al., 1992). Non-human primates such as chimpanzees and pig-tailed macaques can be infected by HIV-1. Although CD4+ cells are not depleted in these systems, the animals are detectably infected by the virus and are useful in determining the efficacy of HIV vaccines. Small animal models include chimeric models that involve the transplantation of human tissue into immunodeficient mice. One such system is the hu-PBL-SCID mouse developed by Mosier et al. (1988). Another is the SCID-hu mouse developed by McCune et al. (1988). Of the two mouse models, the SCID-hu mouse is typically preferred because HIV infection in these animals is more similar to that in humans. SCID-hu mice implanted with human intestine have been shown to be an in vivo model of mucosal transmission of HIV (Gibbons et al., 1997). Methods of constructing mammals with human immune systems are described in U.S. Pat. Nos. 5,652,373, 5,698,767, and 5,709,843.

The animals will be inoculated with the vaccine of the present invention and later challenged with a dose of infectious virus. Efficacy of the vaccine will be determined by methods known by those of skill in the art. Generally, a variety of parameters associated with HIV infection may be tested and a comparison may be made between vaccinated and non-vaccinated animals. Such parameters include viremia, detection of integrated HIV in blood cells, loss of CD4+ cells, production of HIV particles by PBMC, etc. The vaccine will be considered effective if there is a significant reduction of signs of HIV infection in the vaccinated versus the non-vaccinated groups.

The ability of the inactivated HIV particles to elicit neutralizing antibodies can be measured in mice as previously described (LaCasse et al., 1999). The ability of sera to neutralize a range of HIV isolates can be tested using U87-CD4 cells expressing either CCR5 or CXCR4 coreceptors or by using an peripheral blood lymphocyte culture assay (LaCasse et al, 1999, LaCasse et al., 1998; Follis et al., 1998).

4.8 Application in Humans

Of course, the inventor contemplates the application of the present invention as a vaccine to HIV in humans. The inventor contemplates that testing of the present invention as a vaccine in humans will follow standard techniques and guidelines known by those of skill in the art. One important aspect of human application is the production of an effective immune response to the vaccine. Although various ex vivo tests may be performed, such as measuring anti-HIV antibody production and anti-HIV cellular responses, the ultimate test is the ability of the vaccine to prevent infection by HIV or to significantly prolong the onset of AIDS in individuals receiving the vaccine. The monitoring of the efficacy of HIV vaccines in humans is well known to those of skill in the art and the inventor does not contemplate that the present invention would require the development of new methods of testing the efficacy of an HIV vaccine.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Photoaffinity Labels

One compound that may be used to photoinactivate the reverse transcriptase of HIV-1, is an azido dipyridodiazepinona, 9-Azido-5,6-dihydro-11-ethyl-6-methyl-11H-pyrido[2,3-b][1,5]benzodiazepin-5-one (9-AN). Production of 9-AN is described in Hargrave et al. (1991). It may be prepared by mixing an equimolar mixture of 2-chloronicotinic acid and 4-nitrophenylendiamine heated in sulfolane at 170° C. for 5 hours. After cooling, the precipitate is collected and washed with hot ethanol. The obtained mixture of 8- and 9-nitro-5,6-dihydro-11 H-pyrido [2,3-b]benzodizepin-5-ones, are then methylated with methyl iodide and dimsylsodium in DMSO, and the 5,6-dihydro-6-methyl-9nitro isomer is purified by fractional crystallization. The 8-amino compound is obtained by ethylation with ethyl iodide and dimsylsodium in DMSO followed by stannous chloride reduction of the nitro group. The 8-amino compound is then converted to the azide by diazotization with sodium nitrate followed by reaction with sodium azide. The 9-azido derivative is then crystallized form diethyl ether to give analytically pure material: mp 115–118° C.; CIMS molecular ion H* 295; C,H, and N analysis and spectroscopic characterization were consistent with the structure. A methanolic solution of the azido photolabel has a lambda max of 248 nm($\epsilon$=30000).

Another molecule that can be prepared as a photolabel by diazotization is a thiocarboxanilide, known by the trademark name of UC781™ UC781™ was developed by Uniroyal Chemical Ltd. Research laboratories. It is known that UC781™ is a molecule with high affinity for HIV-1 reverse transcriptase and with the characteristics of tight binding. In fact, it is reasonable to assume that UC781™ alone inactivates the HIV-1 reverse transcriptase (Barnard et al., 1997; Borkow et al., 1997). The diazotization of this molecule and its subsequent activation with ultraviolet light further insures the inactivation of the HIV-1 reverse transcriptase. The azido photoaffinity labels, upon exposure to ultraviolet light, transform into highly reactive nitrenes capable of inserting into proximal covalent bonds of the HIV-1 reverse transcriptase enzyme structure.

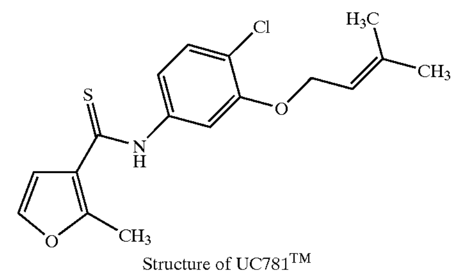

Structure of UC781™

5.2 Example 2

Inactivation of HIV Particles and HIV-Infected Cells

The inactivation of HIV can be accomplished by taking advantage of compounds that bind the HIV reverse transcriptase with a high degree of specificity. Using the technique of photolabeling, a compound with high specific affinity for the HIV-1 reverse transcriptase can then be turned into an "active" moiety which will produce an irreversible inactivation of the reverse transcriptase upon exposure to ultraviolet light irradiation. This inactivation, in the case of the compounds already described and known to have this effect, meets the requirement of being specific for the reverse transcriptase of HIV-1. That is, their labeling and photoactivation is not accompanied by the alteration of any other component of the viral particle than the reverse transcriptase of HIV-1. That is an important element of this invention since the irreversible inactivation of HIV-1 reverse transcriptase will lead to non-infectious particles of HIV-1 with a natural antigenic structure which should behave as the infectious particles of HIV-1 insofar as their capacity for stimulation of an effective immune response. There are many compounds that can be used for the purpose of photolabeling inactivation of the HIV-1 reverse transcriptase and include UC781™ thiocarboxanilide, UC781™ azidothiocarboxanilide, and azido dipyridodiazepinona.

5.2.1 Infection of Virus Producing Cells

Laboratory-adapted and primary wild type HIV isolates will be cultured using established standard techniques. The cells to be used for culture will be phytohemagglutinin (PHA)-stimulated peripheral blood mononuclear cells (PBMC's), since they are more readily infected by both primary isolates and laboratory-adapted isolates than cloned T-cell lines (MT-2 or H9). Briefly, PBMC from normal blood donors are isolated by Ficoll-Hystopaque gradient centrifugation and stimulated with 5 $\mu$g/ml of PHA for three to four days. The PHA-stimulated PBMC are then cultured in RPMI-1640 medium containing 10% heat-inactivated FBS, 100 U penicillin/ml, 100 $\mu$g of streptomycin/ml 2 mM L-glutamine, and 5% purified human interleukin-2.

Aliquots of $10^7$ uninfected PBMC's in 10 ml of medium are pretreated with 2 $\mu$g/ml of polybrene for 1 h at 37° C. The cells are then infected with a 1.0 ml inoculum of cell-free supernatant of the primary isolate or the laboratory-adapted isolate. The infected PBMC's are then resuspended in the culture media and monitored for supernatant p24 antigen concentration, which generally peaks at day 14 postinoculation. The culture supernatants are harvested, pooled, and clarified through a 0.45 μm filter, and aliquoted. The 50% tissue culture infectious dose is determined according to the protocol described by Johnson et al., (1990) using the HIV p24 antigen detection technique.

Of course, the inventor contemplates that the use of PBMCs may not be feasible when large volumes of virus are needed. In this instance, the cell line utilized is MT-2 grown in RPMI 1640 medium with 10% heat-inactivated fetal calf serum (FBS), glutamine and antibiotics. Cells are propagated at 37° C. in an atmosphere of 5% $CO_2$ in air. The virus employed for this work is HIV-1 isolates IIIB and/or RF, which are prepared by an acute infection process. Virus infection of the MT-2 cells is carried out in a bulk infection process. The appropriate number of cells is mixed with infectious virus in a conical centrifuge tube in a small total volume of 1–2 milliliters. Following a 4-hour incubation, the infected cells are brought to the appropriate final concentration of $5\times10^4$ cells per milliliter with fresh tissue culture medium. Uninfected cells at the same concentration are plated for the toxicity controls and for the cell controls. The MOI is adjusted to give complete cell killing in the virus control wells by Day 6. Virus particles are concentrated using standard techniques and quantified using RT assays (Fletcher et al., 1995a, 1995b) and p24 antigen assays.

5.2.2 HIV Particle Inactivation

Once the HIV particles are purified and quantified, the 50% tissue culture infective dose ($[TCID_{50}]=5\times10^4$) is incubated in the presence of four to eight times the 50% inhibitory concentration ($IC_{50}$) of the photoaffinity labeling molecule. In the case of the azido dipyridodiazepinona, the $IC_{50}$ is 160 nM. For the thiocarboxanilide and the azido thiocarboxanilide, the $IC_{50}$ is 0.2 nM. Incubations were in RPMI 1640 without FBS for 2 h at 37° C. with gentle agitation every 15 min. The mixtures of viral particles and photoaffinity labels are exposed to ultraviolet light using a GE 275-W sun lamp that provides a UV-irradiation intensity of about $15\mu W/cm^2$ for a period of at least 50 minutes. After this process, the solution contains particles of HIV-1 with a completely inactivated reverse transcriptase and thus unable to infect susceptible cells.

The infectivity of the inactivated virus particles will be determined by controlled experiments where exposure of susceptible cells to increased concentrations of these particles will fail to produce infection of the cells as evidenced by the sensitive heminested PCR technique described in Yang et al. (1998) and the lack of production of viral particles, reverse transcriptase, and p24. Such a process to assay the production of virus particles is outlined by Borkow et al. (1997). Briefly, 0.5 ml of concentrated inactivated virus is added to 0.5 ml of phytohemagglutinin-activated cord-blood mononuclear cells (CBMC)($4\times10^6$ cells) in RPMI 1640-10% FBS and incubated for 2 h at 37° C. with occasional gentle mixing. The HIV-CBMC incubation mix is diluted with the addition of 10 ml of RPMI 1640, and residual HIV is removed by pelleting the cells at 300×g for 10 min, followed by removal of the supernatant and resuspension of the cells in 2 ml of RPMI 1640-10% FBS containing interleukin-2 (10 U/ml). The entire sample is plated into a single well of a 24-well dish. After 4 days of culture, 1 ml of medium is removed and replaced with 1 ml of fresh medium. On day 7, culture supernatants are isolated and HIV production is assessed by the measurement of RT activity and p24 antigen levels in these cell-free supernatants and cells are be monitored for integration by the heminested PCR technique of Yang et al. (1998).

5.3 Example 3

Production of Noninfectious Nascent Virus from UC781™ -Treated HIV 1 Infected Cells In addition to the inactivation of purified virus, UC781™ has been shown to inactivate nascent virus from HIV-infected cells grown in the presence of the compound (Borkow et al., 1997, incorporated wherein by reference). The methods described by Borkow et al. may be used to produce inactivated virus for use in the present invention. Furthermore, the methods may be used to create a whole-cell vaccine in which the cells are HIV infected but rendered noninfectious by UC781 ™. A whole cell vaccine comprises the injection of HIV-infected cells. The injection of whole cells may provide a more vigorous immune response to the virus. The methods of Borkow et al. (1997) are described below.

5.3.1 Incubation of Chronically HIV-1 Infected H9 Cells with UC781™.

Chronically infected H9 cells ($5\times10^5$ cells) are incubated with 10 μM of UC781™ in a total volume of 1 ml of RPMI 1640-10% FBS for 18 h at 37° C. The cells are then separated from the culture supernatants by centrifugation at 300×g for 10 min. The pelleted H9 cells are washed by suspension in 10 ml of RPMI 1640 followed by centrifugation at 300 ×g for 10 min. The cell pellet is resuspended in 4 ml of RPMI 1640-10% FBS and used in coculture experiments to determine infectivity (Borkow et al., 1997).

5.3.2 Incubation of Peripheral Blood Lymphocytes with UC781™.

Peripheral blood lymphocyte (PBL) cells ($2\times10^6$ cells) isolated from blood of HIV-1-infected patients are incubated with medium and 10 μM UC781™ in a total volume of 1 ml for 2 h at 37° C. Excess drug may be removed by pelleting the cells by centrifugation at 300×g for 10 min and removal of the medium. The cell pellet is washed by suspension in 10 ml of medium followed by centrifugation. This washing step is repeated twice. The final cell pellet is resuspended in 1 ml of medium or another isotonic solution. To insure that the cells are noninfectious, they are cocultured with 1 ml of activated CBMC ($2\times10^6$ cells). The culture medium is changed every 2 days, and fresh activated CBMC ($2\times10^6$ cells) are added once per week. HIV-1 production is monitored by measurement of p24 antigen levels in cell-free culture supernatants. Integration of the virus is tested by the heminested PCR technique of Yang et al. (1998).

5.3 Example 3

Clinical Trial for HIV Vaccine

This example describes a protocol to facilitate an HIV vaccine clinical trial. The various elements of conducting a clinical trial, including patient treatment and monitoring, will be known to those of skill in the art in light of the present disclosure. Generally, the clinical study of the vaccine composed of inactivated viral particles should consist of the administration of such viral particles produced by the photolabeling of reverse transcriptase, as described in the present invention, to human subjects to evaluate safety and cellular, antibody, humoral and other clinical responses. The following information is being presented as a general guideline for use in HIV vaccine clinical trials. Information regarding design of clinical trials can also be obtained in the American Foundation for AIDS Research's HIV Experimental Vaccine Directory, Vol 1, No. 2, June 1998.

5.3.1 Eligible Subjects
 Adult males and females HIV seronegatives.
5.3.2 Subjects Inclusion Criteria
 Patient Age: 18 years–60 years.
5.3.4 Reproductive Criteria
 Negative pregnancy test. Abstinence or effective method of birth control/contraception during the study.
5.3.5 Inclusion Criteria
 The subject must be healthy as defined by a normal physical exam and normal laboratory parameters as defined by the WHO for participants in clinical studies. Subjects must be able to understand and sign an informed consent. Subjects must also have a normal total white blood cell count, lymphocyte, granulocyte and platelet count as well hemoglobin and hematocrit. Subjects must has normal values of the following parameters: urinalysis; BUN; creatinine; bilirubin; SGOT; SGPT; alkaline phosphatase; calcium; glucose; CPK; CD4+ cell count; and normal serum immunoglobulin profile.
5.3.6 Exclusion
 The following are exclusion criteria: HIV-seropositive status; Active drug or alcohol abuse; inability to give an informed consent; medication which may affect immune function with the exception of low dose of nonprescription-strength NSAIDS, aspirin, or acetaminophen for acute conditions such as headache or trauma; any condition which in the opinion of the principal investigator, might interfere with completion of the study or evaluation of the results.
5.3.7 Randomization
 The study will be double blind randomized. The placebo will be the vaccine solution without the inactivated viral particles. Subjects will be assigned randomly to one of the vaccine routes described above.
5.3.8 Dose Range
 Doses of $10^4$, $10^6$ and $10^8$ particles will be studied for clinical safety and immunogenicity. Other does in the range of 10 to $10^{20}$ particles may also be studied.
5.3.10 Administration
 For each dose to be tested, the schedule may consist of administration of a dose on days 0, 30, 60, and a booster dose at 180 days. Route of administration will be intramuscular. Additional routes of administration may include: subcutaneous; oral; intrarectal; intravaginal; intranasal/intramuscular; intrarectal/intramuscular; intranasal/subcutaneous; intrarectal/subcutaneous.
5.3.11 Number of Subjects Per Route of Administration
 There will be 12 subjects per route of administration per dose level. Of the 12 subjects 8 will receive the vaccine and 4 will receive a solution without inactivated viral particles.
5.3.12 Duration of the Study
 24 months.
5.3.13 Endpoints
 The endpoint for clinical safety is no evidence of alteration of the clinical, immunological or laboratory parameters. The endpoint for immunological efficacy is seroconversion with production of an effective cellular, humoral and antibody response against HIV. The effective immunological cellular response can be studied by using cytotoxic T lymphocytes responses against different clashes of HIV. The humoral response can be evaluated by measuring the production of IFN-gamma release using a modified Elispot assay. The antibody production can be assessed by performing neutralization studies against different clades of HIV.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,041,078.
U.S. Pat. No. 5,516,629.
U.S. Pat. No. 5,593,823.
U.S. Pat. No. 5,652,373.
U.S. Pat. No. 5,698,767.
U.S. Pat. No. 5,709,843.
PCT Application No. 91/09603.
Abbas, *Cell*, 84:655, 1996.
Althaus et al., *Biochemistry*, 32(26):6548–6554, 1993.
American Foundation for AIDS Research's HIV Experimental Vaccine Directory, Vol 1, No. 2, June 1998.
Bader, McMahon, Schulz, Narayanan, Pierce, Weislow, Midelfort, Stinson, Boyd, *Proc. Natl. Acad Sci. U.S.A.*, 88:6740–6744, 1991.
Balzarini, Brouwer, Dao, Osika, De Clercq, *Antimicrob. Agents Chemother.*, 40:1454–1466, 1996.
Balzarini, Perez-Perez, Velazquez, San-Felix, Carnarasa, De Clercq, Karlsson, *Proc. Natl. Acad. Sci. U.S.A.*, 92:5470–5474, 1995.
Banchereau and Steinman, "Dendritic cells and the control of immunity," *Nature*, 392:245–252, 1998.
Barnard, Borkow, Parniak, "The Thiocarboxanilide Nonnucleoside UC781 is a Tight-Binding Inhibitor of HIV-1 Reverse Transcriptase," *Biochem.*, 36:7786–7792, 1997.
Bender, Bui, Feldman, Larsson, Bhardwaj, "Inactivated influenza virus, when presented on dendritic cells, elicits human $CD8^+$ cytolytic T cell responses," *J. Exp. Med.*, 1663–1671, 1995.
Blauvelt, Asada, Saville, Klaus-Kovtun, Altman, Yarchoan, Katz, "Productive infection of dendritic cells by HIV-1 and their ability to capture virus are mediated through separate pathways," *J. Clin. Invest.*, 100(8):2043–2053, 1997.
Borkow, Barnard, Nguyen, Belmonte, Wainberg, Parniak, "Chemical Barriers to Human Immunodeficiency Virus Type 1 (HIV-1) Infection: Retrovirucidal Activity of UC781, a Thiocarboxanilide Nonnucleoside Inhibitor of HIV-1 Reverse Transcriptase," *J. of Virol.*, 71(4):3023–3030, 1997.
Buckheit et al., *AIDS Res Hum Retroviruses*, 13(9):789–796, 1997.
Cameron, Pope, Granelli-Piperno, Steinman, "Dendritic cells and the replication of HIV-1," *J. Leukocyte Biol.*, 59:158–171, 1996.
Carlson, McGraw, Keddie, Yee, Rosenthall, Langlois, et al., "Vaccine protection of rhesus macaques against simian immunodeficiency virus infection," *AIDS Res. Hum. Retrovir.*, 6:1239–46, 1990.
Carroll, Olsen, Bennett, Gotlib, Graham, Condra, Stem, Shafer, Kuo, *J. Biol. Chem.*, 268:276–281, 1993.

Cohen, *Science,* 278:25–25, 1997.

Currens et al., *J Pharmacol Exp Ther,* 279(2):652–661, 1996.

Desrosiers, Wyand, Kodama, Ringler, Sehgal, et al., "Vaccine protection against simian immunodeficiency virus infection," *Proc. Natl Acad. Sci. USA,* 86:6353–7, 1989.

Doolittle, "The simian-human connection," *Nature,* 339:338, 1989

Esnouf et al., *Biochem Biophys Res Commun,* 234(2):458–464, 1997.

Fletcher, Arion, Borkow, Wainberg, Dmitrienko, Parniak, "Synergistic inhibition of HIV-1 reverse transcriptase DNA polymerase activity and virus replication in vitro by combinations of carboxanilide nonnucleoside compounds," *Biochem.,* 34:10106–10112, 1995a.

Fletcher, Syed, Methani, Dmitrienko, Parniak, "Carboxanilide derivative nonnucleoside inhibitors of HIV-1 reverse transcriptase interact with different mechanistic forms of the enzyme," *Biochem.,* 34:4036–4042, 1995b.

Follis, Trahey, LaCasse, Nunberg, "Continued utilization of CCR5 Coreceptor by a newly derived T-cell line-adapted isolate of Human Immunodeficiency Virus Type 1," *J. Virol.,* 72:7603–7608, 1998.

Furman et al., *Proc. Natl. Acad. Sci. U.S.A.,* 83:8333–8337, 1986.

Gibbons et al., "Thy/Liv-SCId-Hu mice implanted with human intestine: an in vivo model for investigation of mucosal transmission of HIV," *AIDS Res Hum Retroviruses,* 13(17):1453–1460, 1997.

Goldman, Nunberg, O'Brien, Quintero, Schleif, Freund, Gaul, Saari, Wai, Anderson, Hupe, Emini, Stern, *Proc. Natl. Acad. Sci. U.S.A.,* 88:6863–6867, 1991.

Grob, Wu, Cohen, Ingraham, Shih, Hargrave, McTague, Merluzzi, *AIDS Res. Hum. Retroviruses,* 8:145–152, 1992.

Hardy, "The Human Immunodeficiency Virus," *Medical Clincs of North America,* 80:1239–1261, 1996.

Hargrave et al., *J. of Medicinal Chemistry,* 34:2231–2241, 1991.

Haynes et al., *Science* 271:324–328, 1996.

Ho, Neumann, Perelson, et al., "Rapid turnover of plasma virions and CD4 lymphocytes in HIV-1 infection," *Nature,* 373:123, 1995.

Hu D J, Dondero T J, Rayfield M A, et al., The emerging genetic diversity of HIV: The importance of global surveillance for diagnostics, research, and prevention. JAMA275:210, 1996.

Hwang, Boyle, Lyerly, et al., "Identification of envelope V3 loop as the major determirmnt of CD4 neutralization sensitivity of HIV-1," *Science,* 257:535, 1992.

Johnson et al., "Infectivity assay" In Aldovini a. Walker B. D., eds. *Techniques in HIV research.* New York: Stockton Press:71–76, 1990.

Johnson, Montefiori, Goldstein, Hamm, Zhou, Kitov, et al., "Inactivated whole-virus vaccine derived from a proviral DNA clone of simian immunodeficiency virus induces high levels of neutralizing antibodies and confers protection against heterologous challenge," *Proc. Natl Acad. Sci. USA,* 89:2175–9, 1992a.

Johnston, *Hospital Practice,* 32(5):125–8, 131–40, 1997.

Kindt et al., "Animal models for acquired immunodeficiency syndrome," In *Advances in Immunology,* vol 52. Acedemic Press, Inc., New York, N.Y., 425–474, 1992.

Kleim et al., *Virology,* 231(1):112–118, 1997.

Knight, "Bone-marrow-derived dendritic cells and the pathogenesis of AIDS," *AIDS (Lond.),* 10:807–817, 1996.

LaCasse, Follis, Trahey, Scarborough, Littman, Nunberg, "Fusion-competent vaccines: broad neutralization of primary isolates of HIV," *Science,* 283:357–362, 1999.

LaCasse, Follis, Moudgil, Trahey, Binley, Planelles, Zolla-Pazner, Nunberg, "Coreceptor Utilization by Human Immunodeficiency Virus Type 1 is not a primary determinant of neutralization sensitivity, " *J. Virol.* 72:2491–2495, 1998.

Le Grand, Vogt, Vaslin, Roques, Theodoro, Aubertin, et al., "Specific and non-specific immunity and protection of macaques against SIV infection," *Vaccine,* 10:873–9, 1992.

McCune et al., *Science,* 241:1632–1639, 1988.

Merluzzi, Hargrave, Labadia, Grozinger, Skoog, Wu, Shih, Eckner, Hattox, Adams, Rosethal, Faanes, Echner, Koup, Sullivan, *Sci.,* 20:1411–1413, 1990.

Montefiori and Moore, "Magic of the Occult?" *Science,* 283:336–337, 1999.

Mosier et al., *Nature,* 335:256–259, 1988.

Murphey-Corb, Martin, Davison-Fairburn, Montelaro, Miller, West, et al., "A formalin-inactivated whole SIV vaccine confers protection in macaques," *Science,* 246:1293–7, 1989.

Musey, Hughes, Schacker, Shea, Corey, McElrath, "Cytotoxic T-cell responses, viral load, and disease progression in early human immunodeficiency virus type 1 infection," *N. Eng. J. Med.,* 337(18):1267–1274, 1997.

Oldstone, "HIV versus cytotoxic T lymphocytes—the war being lost," *N. Eng. J. Med.,* 337:1306–1308, 1997.

Osterhaus, de Vries, Morein, Akerblom, Heeney, "Comparison of protection afforded by whole virus ISCOM versus MDP adjuvanated Formalin-inactivated SIV vaccines from i.v. cellfree or cell-associated homologous challenge," *AIDS Res. Hum. Retrovir.,* 8:1507–10, 1992.

Piatak Jr, Sang, Yang, et al., "High levels of HIV-1 in plasma during all stages of infection determined by competitive PCR," *Science,* 259:1749, 1993.

Putkonen, Thorstensson, Cranage, Nilsson, Ghavamzadeh, Albert, et al., "A formalin inactivated whole SIVmac vaccine in Ribi adjuvant protects against homologous and heterologous SIV challenge," *J. Med. Primatol.,* 21:108–12, 1992.

Putkonen, Thorstensson, Walther, Albert, Akerblom, Granquist, et al., "Vaccine protection against HIV-2 infection in cynomolgus monkeys," *AIDS Res. Hum. Retrovir.,* 7:271–7, 1991.

Rosenberg et al., *Science* 278:1447–1450, 1997.

Sabin, "Improbability of effective vaccination against human immunodeficiency virus because of its intracellular transmission and rectal portal of entry," *Proc. Natl. Acad. Sci. USA,* 89:8852–5, 1992.

Schultz, "Changing paradigms for an HIV vaccine," Novel Strategies in the Design and Production of Vaccines Cohen and Shafferman (Eds.) New York, N.Y., *Advances in Experimental Medicine and Biology,* 397:79–90, 1996.

Stanley et al., *N. Engl. J. Med.,* 334:1222, 1996.

Stott and Schild, *Journal of Antimicrobial Chemotherapy* 37, Suppl. B, 185–198, 1996.

Stott, Chan, Mills, Page, Taffs, Cranage, et al., "Preliminary report: protection of cynomologus macaques against simian immunodeficiency virus by a whole fixed cell vaccine," *Lancet,* 336:1538–41, 1990.

Stott, Kitchin, Page, Flanagan, Taffs, Chan, et al., "Anti-cell antibody in macaques," *Nature,* 353:393, 1991.

Sutjipto, Pedersen, Miller, Gardner, Hanson, Gettie, et al., "Inactivated simian immunodeficiency virus vaccine failed to protect rhesus macaques from intravenous or genital mucosal infection but delayed disease in intravenously exposed animals," *J. Virol.,* 64:2290–7, 1990.

Warren and Dolatshahi, "First updated and revised survey of worldwide HIV and SIV vaccine challenge studies in non-human primates: progress in first and second order studies," *J. Med. Primatol.*, 22:203–35, 1993.

Weissman et al., *J. Exp. Med.*, 183:687, 1996.

Yang et al., *Journal of AIDS and Human Retrovirology*, 17:27–34, 1998.

Zhang et al., "Reverse transcription takes place within extracellular HIV-1 virions: potential biological significance," *AIDS Res. Hum. Retroviruses* 9:1287–1296, 1993.

Zhang, Dornadula, Pomerantz, "Endogenous reverse transcription of human immunodeficiency virus type 1 in physiological microenvironments: an important stage for viral infection of nondividing cells," *J. Virol.*, 70:2809–2824, 1996.

What is claimed is:

1. A method of invoking an immune response in an animal which comprises administering to said animal a composition comprising a pharmaceutically-acceptable excipient and an HIV particle comprising inactivated reverse transcriptase, wherein said reverse transcriptase has been inactivated by a method comprising binding said reverse transcriptase with one or more compounds that binds said reverse transcriptase and then irradiating said HIV particles with UV light.

2. The method of claim 1, wherein said immune response is a cellular response.

3. The method of claim 1, wherein said immune response is a humoral response.

4. The method of claim 2, wherein said cellular response comprises CD8+ T cells.

5. The method of claim 2, wherein said cellular response comprises CD4+ T cells.

6. The method of claim 1, wherein said animal is a mammal.

7. The method of claim 1, wherein said mammal is a PBL-SCID mouse or a SCID-hu mouse.

8. The method of claim 6, wherein said mammal is human.

9. The method of claim 1, wherein said animal is HIV-negative.

10. The method of claim 1, wherein said animal is HIV-positive.

11. The method of claim 1, wherein said compound is an azido-labeled compound.

12. The method of claim 11, wherein said azido-labeled compound is azido dipyrodiazepinona or N-[4-chloro-3-(3-methyl-2-butenyloxy)phenyl]-2-methyl-3-furanocarbothiamide.

13. The method of claim 12, wherein said azido-labeled compound is N-[4-chloro-3-(3-methyl-2-butenyloxy)phenyl]-2-methyl-3-furanocarbothiamide.

14. A method of invoking an immune response in an animal which comprises: administering to said animal a composition comprising a pharmaceutically-acceptable excipient and an HIV particle comprising inactivated reverse transcriptase, wherein said reverse transcriptase has been inactivated via binding said reverse transcriptase with at least one compound that binds said reverse transcriptase and then irradiating said HIV particle with UV light.

15. The method of claim 14, wherein said compound is an azido-labeled compound.

16. The method of claim 15, wherein said azido-labeled compound is azido dipyrodiazepinona or N-[4-chloro-3-(3-methyl-2-butenyloxy)phenyl]-2-methyl-3-furanocarbothiamide.

17. The method of claim 16, wherein said azido-labeled compound is N-[4-chloro-3-(3-methyl-2-butenyloxy)phenyl]-2-methyl-3-furanocarbothiamide.

* * * * *

UNITED STATES PATENT AND TRADEMARK OFFICE
CERTIFICATE OF CORRECTION

PATENT NO.   : 6,383,806 B1
DATED        : May 17, 2002
INVENTOR(S)  : Adan Rios It is certified that error appears in the above-identified patent and that said Letters Patent is hereby corrected as shown below:

Column 23,
Line 34, please delete "claim 1" and insert -- claim 6 -- therefor.

Signed and Sealed this

Twenty-fourth Day of September, 2002

Attest:

Attesting Officer

JAMES E. ROGAN
Director of the United States Patent and Trademark Office